(12) United States Patent
Bender et al.

(10) Patent No.: US 9,114,135 B2
(45) Date of Patent: Aug. 25, 2015

(54) SALT COMPOUND

(75) Inventors: Robert Bender, Ottawa (CA); Ho-Lun Joseph Chau, Whistler (CA); Doug Cowart, North Potomac, MD (US)

(73) Assignee: SGC Pharma Inc., Wellesley, MA (US)

( * ) Notice: Subject to any disclaimer, the term of this patent is extended or adjusted under 35 U.S.C. 154(b) by 357 days.

(21) Appl. No.: 13/818,410

(22) PCT Filed: Aug. 24, 2011

(86) PCT No.: PCT/US2011/048966
§ 371 (c)(1),
(2), (4) Date: Jun. 5, 2013

(87) PCT Pub. No.: WO2012/027471
PCT Pub. Date: Mar. 1, 2012

(65) Prior Publication Data
US 2013/0245078 A1    Sep. 19, 2013

Related U.S. Application Data

(60) Provisional application No. 61/376,501, filed on Aug. 24, 2010.

(51) Int. Cl.
C07D 277/24    (2006.01)
A61K 31/426    (2006.01)
A61K 31/194    (2006.01)

(52) U.S. Cl.
CPC ............. *A61K 31/426* (2013.01); *A61K 31/194* (2013.01); *C07D 277/24* (2013.01)

(58) Field of Classification Search
CPC ........................... C07D 277/24; A61K 31/426
See application file for complete search history.

(56) References Cited

U.S. PATENT DOCUMENTS 4,927,819 A      5/1990   Baker et al.
6,310,052 B1 *  10/2001   Thatcher et al. .............. 514/129
7,625,946 B2    12/2009   Piryatinsky et al.

OTHER PUBLICATIONS

International Search Report, PCT/EP2011/048966, dated Jan. 10, 2012, 3 pages.
International Preliminary Report on Patentability, PCT/EP2011/048966, dated Feb. 26, 2013, 6 pages.

* cited by examiner

*Primary Examiner* — Matthew Coughlin
(74) *Attorney, Agent, or Firm* — Lathrop & Gage LLP; Brian C. Trinque

(57) ABSTRACT

A salt compound, and methods for mitigating neurodegeneration, effecting neuroprotection and/or effecting cognition enhancement in a subject using the salt compound are described. Neurological or cognitive conditions are treated by administering to a subject an effective amount of a therapeutic salt compound comprising a nitrate ester.

16 Claims, 1 Drawing Sheet

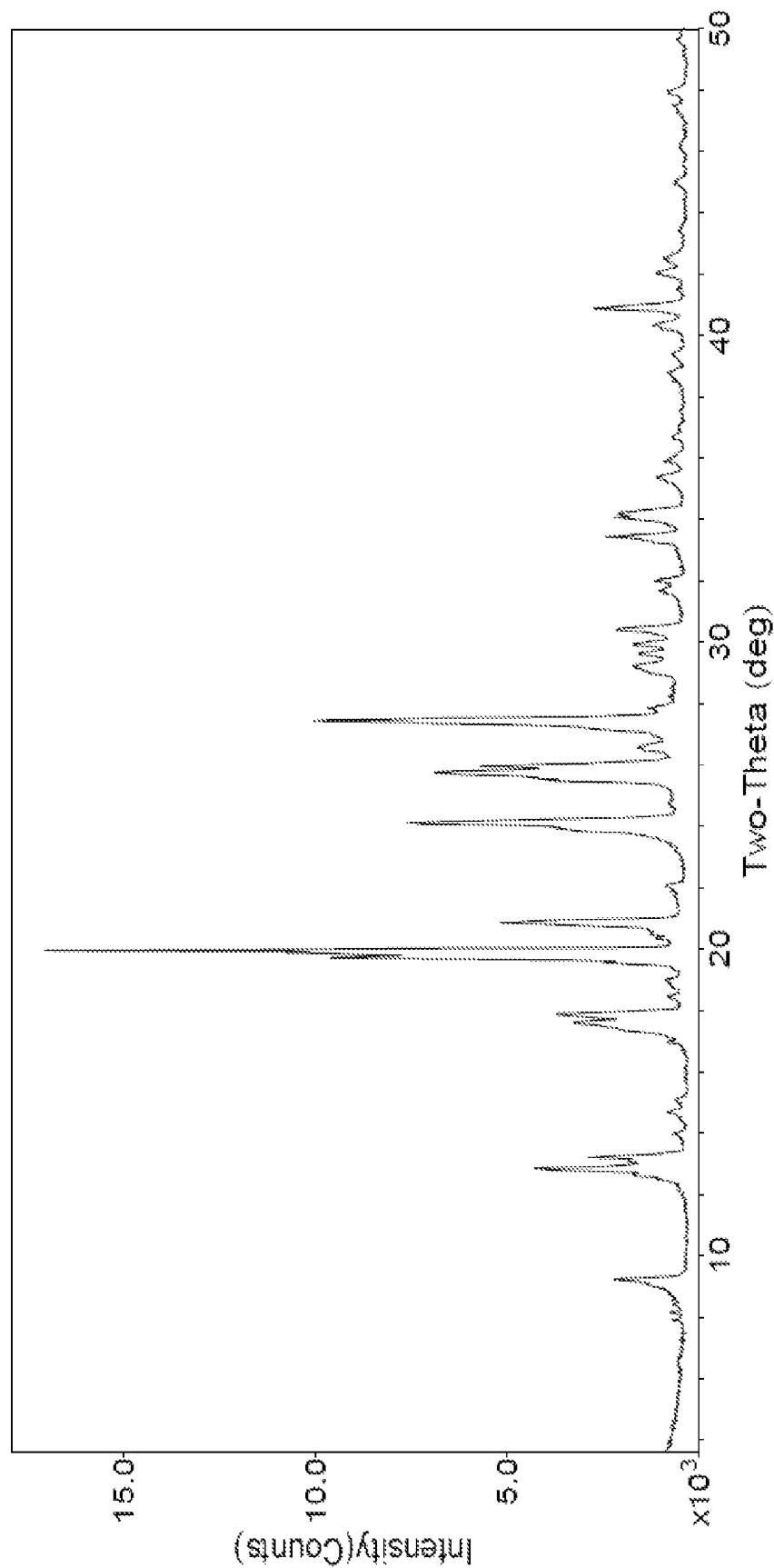

SALT COMPOUND

RELATED APPLICATIONS

This application is a 35 U.S.C. §371 filing of International Patent Application No: PCT/US2011/048966, filed on Aug. 24, 2011, and which claims priority to U.S. Provisional Patent Application No: 61/376,501, filed Aug. 24, 2010. The entire contents of the aforementioned applications are hereby incorporated herein by reference.

BACKGROUND OF THE INVENTION

The compound 2-(4-methylthiazol-5-yl)ethyl nitrate:

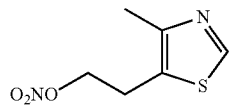

is known to interact with amino acid neurotransmitter receptors such as the NMDA receptor and the γ-aminobutyric acid type A (GABA$_A$) receptor. This compound is also known to stimulate cerebral soluble guanylyl cyclase (GCase). As such, this compound is useful for its neuroprotective properties, and effecting cognition enhancement. See, e.g., U.S. Pat. No. 6,310,052. It has been found that new solid forms of 2-(4-methylthiazol-5-yl)ethyl nitrate can be prepared as the maleate salt form. This salt form exhibits new physical properties that can be exploited in order to achieve new properties, making it useful as a drug substance.

SUMMARY OF THE INVENTION

Accordingly, the present invention provides the maleate salt of the compound

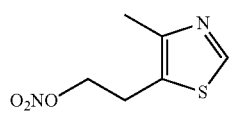

(also referred to herein as "2-(4-methylthiazol-5-yl)ethyl nitrate maleate salt," "the maleate salt of 2-(4-methylthiazol-5-yl)ethyl nitrate," or "the salt compound"). Another object of the present invention is to provide methods for making 2-(4-methylthiazol-5-yl)ethyl nitrate maleate salt. Another object of the invention is to provide methods for effecting neuroprotection, mitigating neurodegeneration and/or effecting cognition enhancement employing 2-(4-methylthiazol-5-yl)ethyl nitrate maleate salt. Another object of the present invention is to provide 2-(4-methylthiazol-5-yl)ethyl nitrate maleate salt as a neuroprotective agent. Yet another object of the present invention is to provide 2-(4-methylthiazol-5-yl)ethyl nitrate maleate salt for use in cognition enhancement.

In another aspect, provided herein is a pharmaceutical composition comprising the maleate salt of the compound

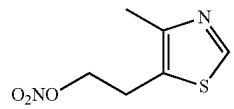

together with a pharmaceutically acceptable diluent or carrier.

Also provided herein is a dry tablet composition comprising the maleate salt of the compound

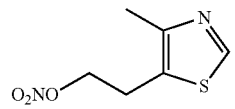

and a pharmaceutically acceptable diluent or carrier. The dry tablet can be formulated for oral administration.

In still another aspect, provided herein is a method for inhibiting neurodegeneration, or effecting neuroprotection in a subject in need thereof, said method comprising administering to said subject an effective amount of the salt compound or pharmaceutical composition described above, such that said neurodegeneration is inhibited or said neuroprotection is affected. In one embodiment, administering the therapeutic compound to said subject modulates levels of cyclic nucleotide cGMP and/or cAMP.

The neurodegeneration or said neuroprotection that is treated can be associated with a condition selected from the group consisting of stroke, Parkinson's disease, Alzheimer's disease, Huntington's disease, multiple sclerosis, amyotrophic lateral sclerosis, AIDS-induced dementia, epilepsy, alcoholism, alcohol withdrawal, drug-induced seizure, viral/bacterial/fever-induced seizure, trauma to the head, hypoglycemia, hypoxia, myocardial infarction, cerebral vascular occlusion, cerebral vascular hemorrhage, hemorrhage, an environmental excitotoxin, dementia, trauma, drug-induced brain damage, and aging. In another embodiment, said neurodegeneration or said neuroprotection is associated with dementia. In still another embodiment, said neurodegeneration or said neuroprotection is associated with Alzheimer's disease.

In one embodiment, the salt compound or pharmaceutical composition inhibits dementia. In another embodiment, the salt compound or pharmaceutical composition inhibits Alzheimer's disease. Thus, in one embodiment, provided herein is a method of treating Alzheimer's disease in a subject in need thereof, comprising administering to the subject an effective amount of the maleate salt of 2-(4-methylthiazol-5-yl)ethyl nitrate.

In another embodiment, provided herein is a method for effecting cognition enhancement in a subject in need thereof comprising administering to said subject an effective amount the salt compound or pharmaceutical composition described above.

In another aspect, provided herein is a method for mitigating cerebral damage due to ischemia in a subject in need thereof comprising administering to said subject an effective amount of the salt compound or pharmaceutical composition described above, such that cerebral damage is mitigated.

In certain embodiments of the treatments described above, the salt compound or pharmaceutical composition is administered orally. In a particular embodiment of these treatments, the salt compound or pharmaceutical composition is administered in as a dry tablet.

BRIEF DESCRIPTION OF THE DRAWINGS

FIG. 1 shows an XRPD graphic scan of 2-(4-methylthiazol-5-yl)ethyl nitrate maleate salt.

DETAILED DESCRIPTION OF INVENTION

This invention pertains to a salt compound useful for treating neurodegeneration. The methods of the invention involve administering to a subject 2-(4-methylthiazol-5-yl)ethyl nitrate maleate salt, which effects neuroprotection and/or cognition enhancement. Without being bound by theory, neuroprotection and/or cognition enhancement can be effected, for example, by modulating an interaction with guanylyl cyclase (GCase), a glutamate or non-glutamate neuroreceptor or attenuating free radical damage. GCase is the enzyme responsible for cGMP production in various areas of the brain.

Neurodegeneration is mitigated by stimulating cerebral GCase. One of the major targets for organic nitrates is GCase activation, resulting in the production of cGMP. Experimental evidence obtained in a number of in vitro model systems supports the notion that elevated levels of cGMP help to prevent apoptotic (programmed) cell death. Thus, a cGMP-dependent mechanism significantly increases the survival of trophic factor-deprived PC12 cells and rat sympathetic neurons (Farinelli et al., 1996), and of primary cultures of rat embryonic motor neurons (Estevez et al., 1998). The mechanism of action for organic nitrates in preventing apoptotic cell death may be inhibition of caspase-3 activation indirectly through elevations in cGMP levels or directly via protein S-nitrosylation of the enzyme by an NO-intermediate (Kim et al., 1997). Caspase-3 is a member of the cysteine protease family of enzymes that are essential for the execution step in apoptosis (Cohen, 1997; Nicholson and Thornberry, 1997). Activation of caspase-3 is required for apoptotic cell death in trophic factor-deprived PC12 cells (Haviv et al., 1997) and in glutamate-mediated apoptotic cell death of cultured cerebellar granule neurons (Du et al., 1997). In animal models of cerebral ischemia, caspase-3 activity is induced and may be responsible for the apoptotic component of delayed neuronal cell death (Chen et al., 1998; Namura et al., 1998; Ni et al., 1998). Inhibitors of caspase-3 significantly decrease the apoptotic component of delayed neuronal cell death in response to ischemic injury both in vitro (Gottron et al., 1997) and in vivo (Endres et al., 1998). A secreted region of the Alzheimer's disease β-amyloid precursor protein lowers intracellular calcium levels and provides neuroprotective effects on target cells through increases in cGMP levels and activation of protein kinase G (Barger et al., 1995; Furukawa et al., 1996). In preferred embodiments of the methods of the invention, the salt compound has the capacity to activate GCase directly or via release of an NO-containing intermediate are used to modulate GCase activity.

According to certain other aspects of the invention, cognition enhancement (e.g., improved memory performance) is achieved by stimulating cerebral GCase. Several lines of experimental evidence support the notion that GCase and cGMP are involved in the formation and retention of new information. cGMP has been directly implicated in both long-term potentiation (LTP) and long-term depression (LTD), which are proposed cellular models for learning and memory (Arancio et al., 1995; Wu et al., 1998). In animal models, elevation of hippocampal cGMP levels leading to increased protein kinase G activity has been shown to be important for retention and consolidation of new learning (Bernabeu et al., 1996, 1997). Thus, stimulation of cerebral GCase activity is expected to improve learning and memory performance in individuals in whom cognitive abilities are impaired by injury, disease, or aging.

Organic nitrate esters have differential effects to activate soluble GCase and to cause cGMP accumulation in vascular and brain tissue (see, e.g., U.S. Pat. No. 6,310,052). There is a clear dissociation between the vascular relaxation effects of organic nitrate esters and ability to effect neuroprotection. Activation of GCase and accumulation of cGMP have been shown to be important in the neuroprotection of hippocampal brain slices subjected to a period of in vitro ischemia.

Cerebral ischemia results in marked increases in the release of the excitatory amino acid glutamate in the affected brain region (Bullock et al., 1998; Huang et al., 1998; Yang et al., 1998). In both humans (Bullock et al., 1998) and experimental animals (Huang et al., 1998; Goda et al., 1998; Yang et al., 1998), the amount of glutamate released during ischemia is positively correlated with the extent of brain injury. In experimental animal models of cerebral ischemia, decreased release of glutamate during ischemia (Goda et al., 1998) or blockade of glutamate receptors with antagonists (Ibarrola et al., 1998; O'Neill et al., 1998; Umemura et al., 1997) significantly reduces the extent of brain injury. However, these interventions are only effective when given prior to or during the ischemic insult. To be broadly useful, a therapeutic intervention is preferably effective when administered after the period of ischemia.

Accordingly, the salt compound provided herein can be used for treatment of conditions including, but not limited to: stroke; Parkinson's disease; Alzheimer's disease; Huntington's disease; multiple sclerosis; amylotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitotoxins of plant, animal and marine origin; and the like.

The direct effects of organic nitrates on amino acid neurotransmitter receptors has been tested using the *Xenopus oocyte* expression system and two-electrode voltage-clamp recording methods (see, e.g., U.S. Pat. No. 6,310,052). Organic nitrates have been found to have direct, modulatory effects on $GABA_A$ receptor function. These allosteric modulatory effects of organic nitrates were not shared by direct NO-generating compounds, indicating a novel mechanism of action for organic nitrates to interact with $GABA_A$ receptors. In behavioural models of learning and memory, drugs which decrease $GABA_A$ receptor function improve performance on learning and memory tasks (Venault et al., 1992). Thus, the behavioural effect of organic nitrates, developed to act as modulators of $GABA_A$ receptor function, will be to improve memory performance and cognition in patient populations. It will be appreciated, therefore, that these organic nitrates can be used for treatment of conditions including but not limited to: stroke; dementias of all type; trauma; drug-induced brain damage; and aging.

According to certain aspects of the invention, neurodegeneration is mitigated by inhibition of free radical damage. Reoxygenation and reperfusion after a period of ischemia contributes significantly to the development of brain injury. Oxygen radicals, especially superoxide and peroxynitrite, formed in the period after an ischemic event may initiate processes such as breakdown of membrane lipids (lipid peroxidation), leading to loss of cell membrane integrity and inhibition of mitochondrial function (Macdonald and Stoodley, 1998; Gaetani et al, 1998). Oxidative stress is also believed to be one factor involved in initiation of apoptotic neuronal cell death (Tagami et al., 1998). In experimental animal models of ischemic brain injury, free radical scavengers and enhanced activity of superoxide dismutase have been found to reduce the extent of neuronal injury and cell death (Chan et al., 1998; Mizuno et al., 1998; Tagami et al., 1998). In preferred embodiments of the methods of the invention, the slat compound has the capacity to inhibit production of free radicals and/or act as a free radical scavenger, thereby attenuating the brain injury that occurs after a period of cerebral ischemia. It will be appreciated by those skilled in the art, that any organic nitrate in which vasodilatory potency is reduced and neuroprotective potency increased, represents a new and useful therapeutic agent for use in neuroprotection, particularly in treatment of conditions including but not limited to: stroke; Parkinson's disease; Alzheimer's disease; Huntington's disease; multiple sclerosis; amylotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitotoxins of plant, animal and marine origin. GTN itself, proposed as a neuroprotective agent, has no clinical utility as a neuroprotective agent in therapy owing to its extraordinarily high vasodilatory potency. Similarly, by extrapolation, 1,2,3-trinitratopropane (GTN) derivatives are not expected to have clinical utility as neuroprotective agents in therapy owing to their especially high vasodilatory potency.

It will additionally be appreciated by those skilled in the art that the use in therapy of 2-(4-methylthiazol-5-yl)ethyl nitrate maleate salt in cognition enhancment, represents a new and useful treatment for cognition enhancement, particularly in treatment of conditions including but not limited to: stroke; dementias of all type, trauma, drug-induced brain damage, and aging.

"Mitigating neurodegeneration" as used herein involves effecting neuroprotection, inhibiting or preventing neurodegeneration, and/or ameliorating the manifestations or impact of neurodegeneration. Such amelioration includes effecting cognition enhancement, as is quantified by tests known in the art (e.g., Venault et al., 1992, incorporated herein by reference). "Modulating" a biological process as used herein (for example, modulating the activity of the non-glutamate neuroreceptors), encompasses both increasing (positively modulating) and decreasing (negatively modulating) such activity, and thus inhibition, potentiation, agonism, and antagonism of the biological process.

In one aspect, the invention provides a method of treating a neurological condition and/or preventing an undesirable mental condition (e.g., memory loss) including the step of administering to a subject an effective amount of 2-(4-methylthiazol-5-yl)ethyl nitrate maleate salt. In one embodiment, the therapeutic compound is capable of effecting neuroprotection. In another embodiment of the invention, the therapeutic compound is capable of effecting cognition enhancement.

In the methods of the invention, neurodegeneration in a subject is mitigated, and/or neuroprotection and/or cognition enhancement is effected, by administering a therapeutic compound of the invention to the subject. The term "subject" is intended to include living organisms in which the particular neurological condition to be treated can occur. Examples of subjects include humans, apes, monkeys, cows, sheep, goats, dogs, cats, mice, rats, and transgenic species thereof. As evidenced by Mordenti (1986) and similar articles, dosage forms for animals such as, for example, rats can be and are widely used directly to establish dosage levels in therapeutic applications in higher mammals, including humans.

In particular, the biochemical cascade initiated by cerebral ischemia is generally accepted to be identical in mammalian species (Mattson and Scheff, 1994; Higashi et al., 1995). In light of this, pharmacological agents that are neuroprotective in animal models such as those described herein are believed to be predictive of clinical efficacy in humans, after appropriate adjustment of dosage. Specifically, there are comparable memory-deficit patterns between brain-damaged rats and humans, which indicates that the rat can serve as an excellent animal model to evaluate the efficacy of pharmacological treatments or brain damage upon memory (Kesner, 1990). An approved drug for the clinical treatment of occlusive stroke in humans is a tissue plasminogen activator, which is administered at a dose of 0.9 mg/kg by intravenous injection (Wittkowsky, 1998). This drug is also effective in protecting the rat brain subjected to cerebral ischemia by occlusion of the middle cerebral artery, when administered at a dose of 10 mg/kg intravenously Giang et al., 1998).

As would also be apparent to a person skilled in the art, the invention further encompasses methods of the invention employed ex vivo or in vitro. Also, diagnostic tests or studies of efficacy of selected compounds may conveniently be performed ex vivo or in vitro, including in animal models. Such tests, studies and assays are within the scope of the invention.

Administration of the salt of the present invention to a subject to be treated can be carried out using known procedures, at dosages and for periods of time effective to mitigate neurodegeneration, and/or to effect neuroprotection and/or cognition enhancement in the subject. An effective amount of the therapeutic compound necessary to achieve a therapeutic effect may vary according to factors such as the amount of neurodegeneration that has already occurred at the clinical site in the subject, the age, sex, and weight of the subject, and the ability of the therapeutic compound to mitigate neurodegeneration and/or to effect neuroprotection and/or cognition enhancement in the subject. Dosage regimens can be adjusted to provide the optimum therapeutic response. For example, several divided doses may be administered daily or the dose may be proportionally reduced as indicated by the exigencies of the therapeutic situation. A non-limiting example of an effective dose range for a therapeutic salt of the invention is between 0.5 and 500 mg/kg of body weight per day. In an aqueous composition, preferred concentrations for the active compound (i.e., the therapeutic compound that can mitigate neurodegeneration and/or effect neuroprotection and/or cognition enhancement) are between 5 and 500 mM, more preferably between 10 and 100 mM, and still more preferably between 20 and 50 mM.

The therapeutic compounds of the invention can be effective when administered orally. Accordingly, a preferred route of administration is oral administration. Alternatively, the active compound may be administered by other suitable routes such as transdermal, subcutaneous, intraocular, intravenous, intramuscular or intraperitoneal administration, and the like (e.g., by injection). Depending on the route of administration, the active compound may be coated in a material to protect the compound from the action of acids, enzymes and other natural conditions which may inactivate the compound.

The compounds of the invention can be formulated to ensure proper distribution in vivo. For example, the blood-brain barrier (BBB) excludes many highly hydrophilic compounds. To ensure that the therapeutic compounds of the invention cross the BBB, they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs ("targeting moieties"), thus providing targeted drug delivery (see, e.g., Ranade et al., 1989). Exemplary targeting moieties include folate and biotin (see, e.g., U.S. Pat. No. 5,416,016 to Low et al.); mannosides (Umezawa et al., 1988); antibodies (Bloeman et al., 1995; Owais et al., 1995); and surfactant protein A receptor (Briscoe et al., 1995). In a preferred embodiment, the therapeutic compounds of the invention are formulated in liposomes; in a more preferred embodiment, the liposomes include a targeting moiety.

It will be appreciated that the ability of a compound of the invention to mitigate neurodegeneration will, in certain embodiments, be evaluated by observation of one or more symptoms or signs associated with neurodegeneration in vivo. Thus, for example, the ability of a compound to mitigate neurodegeneration may be associated with an observable improvement in a clinical manifestation of the underlying neurodegeneration-related disease state or condition, or a slowing or delay in progression of symptoms of the condition. Thus, monitoring of clinical manifestations of disease can be useful in evaluating the neurodegeneration-mitigating efficacy of a compound of the invention.

The method of the invention is useful for treating neurodegeneration associated with any disease in which neurodegeneration occurs. Clinically, neurodegeneration can be associated with conditions including but not limited to: stroke; Parkinson's disease; Alzheimer's disease; Huntington's disease; multiple sclerosis; amylotrophic lateral sclerosis; AIDS-induced dementia; epilepsy; alcoholism; alcohol withdrawal; drug-induced seizures; viral/bacterial/fever-induced seizures; trauma to the head; hypoglycemia; hypoxia; myocardial infarction; cerebral vascular occlusion; cerebral vascular hemorrhage; hemorrhage; environmental excitotoxins of plant; animal and marine origin; dementias of all type; trauma; drug-induced brain damage; and aging; or result from surgical procedures such as cardiac bypass.

The term "subject" is intended to include animals, which are capable of suffering from or afflicted with neurodegeneration. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from neurodegeneration.

Pharmaceutical Compositions

The maleate salt compound of the invention can be administered in a pharmaceutically acceptable vehicle. As used herein, "pharmaceutically acceptable vehicle" includes any and all solvents, excipients, dispersion media, coatings, antibacterial and antifungal agents, isotonic and absorption delaying agents, and the like that are compatible with the activity of the compound and are physiologically acceptable to the subject. An example of the pharmaceutically acceptable vehicle is buffered normal saline (0.15 M NaCl). The use of such media and agents for pharmaceutically active substances is well known in the art. Except insofar as any conventional media or agent is incompatible with the therapeutic compound, use thereof in the compositions suitable for pharmaceutical administration is contemplated. Supplementary active compounds can also be incorporated into the compositions.

In a particular embodiment, provided herein is 2-(4-methylthiazol-5-yl)ethyl nitrate maleate salt formulated in a pharmaceutical composition together with a pharmaceutically acceptable diluent or carrier.

In one embodiment, the salt compound is formulated into a dry tablet. The dry tablet can include a mixture of active substances and excipients, such as excipients in powder form, pressed or compacted into a solid. Examples of appropriate excipients for a dry tablet include, but are not limited to, disintegrants, diluents, lubricants, binders, granulating agents, glidants, sweeteners or other flavors, and pigments. The dry tablet can also include a polymer coating that can make the tablet smoother and easier to swallow, to control the release rate of the active ingredient, to make it more resistant to the environment (extending its shelf life), or to enhance the tablet's appearance.

The maleate salt provided herein has processing advantages over other salts (e.g., the chloride, phosphate, mesylate, and sulfate salts) in the preparation of a dry tablet.

The dry tablet can be used for oral administration. The dry tablet can also be administered sublingually, buccally, rectally or intravaginally.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

In one embodiment, the maleate salt compound is formulated with methocel K100M, avicel PH 102, providone, cab-o-sil, and magnesium stearate. In another embodiment, the pharmaceutical composition comprises, by weight, 20%-60% 2-(4-methylthiazol-5-yl)ethyl nitrate maleate salt, 30%-40% methocel K100M, 20%-30% avicel PH 102, 1%-15% providone, 0.1%-1% cab-o-sil, and 0.1%-1% magnesium stearate. In another embodiment, the pharmaceutical composition comprises, by weight, approximately 30% 2-(4-methylthiazol-5-yl)ethyl nitrate maleate salt, approximately 35% methocel K100M, approximately 23% avicel PH 102, approximately 10% providone, approximately 0.25% cab-o-sil, and approximately 0.5% magnesium stearate. In another embodiment, the pharmaceutical composition comprises, by weight, approximately 40% 2-(4-methylthiazol-5-yl)ethyl nitrate maleate salt, approximately 25% methocel K100M, approximately 23% avicel PH 102, approximately 10% providone, approximately 0.25% cab-o-sil, and approximately 0.5% magnesium stearate. In a particular embodiment, the pharmaceutical compositions provided above are formulated into a dry tablet.

In another embodiment, the maleate salt compound is formulated with ethocel 100 premium, avicel PH 102, providone, cab-o-sil, and magnesium stearate. In another embodiment, the pharmaceutical composition comprises, by weight, 30%-60% 2-(4-methylthiazol-5-yl)ethyl nitrate maleate salt, 20%-50% ethocel 100 premium, 20%-30% avicel PH 102, 1%-15% providone, 0.1%-1% cab-o-sil, and 0.1%-1% magnesium stearate. In another embodiment, the pharmaceutical composition comprises, by weight, approximately 40% 2-(4-methylthiazol-5-yl)ethyl nitrate maleate salt, approximately 25% ethocel 100 premium, approximately 23% avicel PH 102, approximately 10% providone, approximately 0.25% cab-o-sil, and approximately 0.5% magnesium stearate. In a particular embodiment, the pharmaceutical compositions provided above are formulated into a dry tablet.

The salt compound can also be formulated into a "controlled-release" formulation, which includes dosage forms whose drug-release characteristics of time course and/or location are chosen to accomplish therapeutic or convenience objectives not offered by conventional dosage forms such as a solution or an immediate release dosage form. In a particular embodiment, provided herein is a dry tablet comprising a controlled-release formulation of 2-(4-methylthiazol-5-yl) ethyl nitrate maleate salt.

The therapeutic compound may also be administered parenterally (e.g., intramuscularly, intravenously, intraperitoneally, intraspinally, or intracerebrally). Dispersions can be prepared in glycerol, liquid polyethylene glycols, and mixtures thereof and in oils. Under ordinary conditions of storage and use, these preparations may contain a preservative to prevent the growth of microorganisms. Pharmaceutical compositions suitable for injectable use include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. The vehicle can be a solvent or dispersion medium containing, for example, water, ethanol, polyol (for example, glycerol, propylene glycol, liquid polyethylene glycol, and the like), suitable mixtures thereof, and vegetable oils. The proper fluidity can be maintained, for example, by the use of a coating such as lecithin, by the maintenance of the required particle size in the case of dispersion, and by the use of surfactants.

Prevention of the action of microorganisms can be achieved by various antibacterial and antifungal agents, for example, parabens, chlorobutanol, phenol, ascorbic acid, thimerosal, and the like. In some cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filter sterilization. Generally, dispersions are prepared by incorporating the therapeutic compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient (i.e., the therapeutic compound) optionally plus any additional desired ingredient from a previously sterile-filtered solution thereof.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of neurological conditions in subjects.

Therapeutic compositions can be administered in time-release or depot form, to obtain sustained release of the therapeutic compounds over time. The therapeutic compounds of the invention can also be administered transdermally (e.g., by providing the therapeutic compound, with a suitable carrier, in patch form).

Active compounds are administered at a therapeutically effective dosage sufficient to mitigate neurodegeneration and/or to effect neuroprotection and/or cognition enhancement in a subject. A "therapeutically effective dosage" preferably mitigates neurodegeneration by about 20%, more preferably by about 40%, even more preferably by about 60%, and still more preferably by about 80% relative to untreated subjects. The ability of a compound to mitigate neurodegeneration can be evaluated in model systems that may be predictive of efficacy in mitigating neurodegeneration in human diseases, such as animal model systems known in the art (including, e.g., the method of transient middle cerebral artery occlusion in the rat) or by in vitro methods, (including, e.g., the assays described herein).

Carrier or substituent moieties useful in the present invention may also include moieties that allow the therapeutic compound to be selectively delivered to a target organ. For example, delivery of the therapeutic compound to the brain may be enhanced by a carrier moiety using either active or passive transport (a "targeting moiety"). Illustratively, the carrier molecule may be a redox moiety, as described in, for example, U.S. Pat. Nos. 4,540,654 and 5,389,623, both to Bodor. These patents disclose drugs linked to dihydropyridine moieties which can enter the brain, where they are oxidized to a charged pyridinium species which is trapped in the brain. Thus drugs accumulate in the brain. Other carrier moieties include compounds, such as amino acids or thyroxine, which can be passively or actively transported in vivo. Such a carrier moiety can be metabolically removed in vivo, or can remain intact as part of an active compound. Structural mimics of amino acids (and other actively transported moieties) including peptidomimetics, are also useful in the invention. As used herein, the term "peptidomimetic" is intended to include peptide analogues which serve as appropriate substitutes for peptides in interactions with, for example, receptors and enzymes. The peptodomimetic must possess not only affinity, but also efficacy and substrate function. That is, a peptidomimetic exhibits functions of a peptide, without restriction of structure to amino acid constituents. Peptidomimetics, methods for their preparation and use are described in Morgan et al. (1989), the contents of which are incorporated herein by reference. Many targeting moieties are known, and include, for example, asialoglycoproteins (see e.g., Wu, U.S. Pat. No. 5,166,320) and other ligands which are transported into cells via receptor-mediated endocytosis (see below for further examples of targeting moieties which may be covalently or non-covalently bound to a target molecule).

The compound 2-(4-methylthiazol-5-yl)ethyl nitrate maleate salt can be synthesized by methods set forth herein (see, e.g., Working Examples) or as described in U.S. Pat. Nos. 5,807,847; 5,883,122; and 6,310,052. Various compounds for use in the methods of the invention are commercially available and/or can be synthesized by standard techniques. In general, nitrate esters can be prepared from the corresponding alcohol, oxirane or alkene by standard methods, that include:

nitration of alcohols and oxiranes, mixed aqueous/organic solvents using mixtures of nitric and sulfuric acid and/or their salts, with temperature control (see Yang et al., 1996); nitration of alcohols and oxiranes in acetic anhydride using nitric acid or its salts with or without added acid catalyst, with temperature control (see, e.g., Louw et al., 1976); nitration of an alcohol with a nitronium salt, e.g. a tetrafluoroborate; nitration of an alkene with thallium nitrate in an appropriate solvent (see Ouellette et al., 1976).

The following Examples further illustrate the present invention and are not intended to be limiting in any respect. Those skilled in the art will recognize, or be able to ascertain using no more than routine experimentation, numerous equivalents to the specific procedures described herein. Such equivalents are considered to be within the scope of this invention and are covered by the claims.

WORKING EXAMPLES

Synthesis of 2-(4-methylthiazol-5-yl)ethyl nitrate maleate salt

The synthesis of 2-(4-methylthiazol-5-yl)ethyl nitrate can be found in U.S. Pat. No. 6,310,052 (Example 14), which is incorporated herein by reference in its entirety. The synthetic route employed for synthesis of 2-(4-methylthiazol-5-yl) ethyl nitrate maleate salt is shown below:

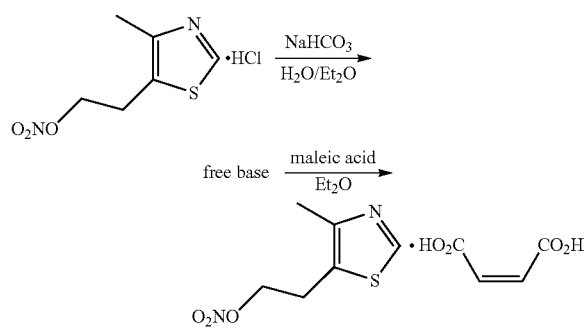

$^1$H-NMR Spectroscopy

Nuclear magnetic resonance spectra were recorded on a Bruker AM 400 Instrument at ambient temperature for 2-(4-methylthiazol-5-yl)ethyl nitrate maleate salt. The $^1$H-NMR spectrum and assignment are shown below (in $D_2O$), which conforms to the structure of 2-(4-methylthiazol-5-yl)ethyl nitrate maleate salt.

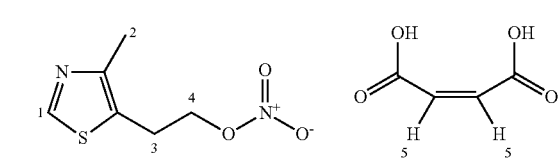

| $^1$H-NMR Measurement | | | |
|---|---|---|---|
| Chemical shifts (δ) | No. of protons | Peak patterns | Peak Assignments |
| 2.38 | 3 | s | $H_2$ |
| 3.24 | 2 | t | $H_3$ |
| 4.64 | 2 | t | $H_4$ |
| 6.29 | 2 | s | $H_5$ |
| 8.88 | 1 | s | $H_1$ |

$^{13}$C-NMR Spectroscopy

Broadband decoupled $^{13}$C-NMR spectrum was recorded for 2-(4-methylthiazol-5-yl)ethyl nitrate maleate salt (in $D_2O$). The $^{13}$C-NMR Spectrum and assignment are shown below, which conforms to the structure of 2-(4-methylthiazol-5-yl)ethyl nitrate maleate salt.

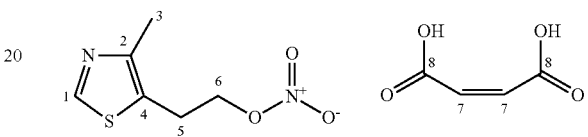

| $^{13}$C-NMR Measurement | | |
|---|---|---|
| Chemical shifts (δ) | Number of carbons | Peak assignments |
| 13.01 | 1 | $C_3$ |
| 23.51 | 1 | $C_5$ |
| 72.41 | 1 | $C_6$ |
| 126.97 | 1 | $C_4$ |
| 130.75 | 1 | $C_7$ |
| 149.25 | 1 | $C_2$ |
| 151.92 | 1 | $C_1$ |
| 167.81 | 1 | $C_8$ |

Mass Spectrometry

Electrospray ionization mass spectrometry (ESI-MS) analyses were carried out on a Micromass ZQ-4000 single quadruple mass spectrometer (Milford, Mass., USA) with positive ion charge. Samples were suspended in ethanol and infused by a syringe pump at 10 μL/min. The Micromass ZQ-4000 is a high resolution/accurate mass instrument with positive and negative ion capability with a mass range of 2000 Daltons at 10 kv. The MS spectrum and assignment for 2-(4-methylthiazol-5-yl)ethyl nitrate maleate salt conformed to the structure of 2-(4-methylthiazol-5-yl)ethyl nitrate maleate salt.

DSC and TGA Testing

DSC Methodology: The Perkin Elmer Pyris Diamond Differential Scanning calorimeter was calibrated for temperature and energy with high-purity indium and zinc. A 5-8 mg sample was precisely weighted and sealed into an aluminum pan. The measurement was performed at a heating rate of 20° K/min in a high purity nitrogen atmosphere. The result is shown below.

TGA Methodology: The Perkin Elmer Pyris 1 Thermogravimetric Analyzer was calibrated for temperature and weight using standard materials. About 3-5 mg sample was taken for testing. The measurement was carried out at a heating rate of 20° K/min in a high purity nitrogen atmosphere.

X-Ray Powder Diffraction

A thermo ARL X'tra powder diffractometer with Cu radiation λ=0.1542 nm was used. The measurement conditions were changed from standard to high resolution and over an extended collection period to improve detect ability of potential crystalline impurities. The samples were analyzed as-is, with no grinding or other pre-treatment conducted prior to analysis. Analyses were performed from 3-50 degree 2-theta using the following conditions: divergence slit: 0.9 mm; anti-scatter slit: 0.3 mm; receiving slit: 0.1 mm; detector slit: 0.6 mm; scan rate: 3 degree/min. A typical XRPD graphic scan of 2-(4-methylthiazol-5-yl)ethyl nitrate maleate salt is shown in FIG. 1.

Formulations

The compound 2-(4-methylthiazol-5-yl)ethyl nitrate maleate salt was formulated as follows:

| Component | % | g |
|---|---|---|
| 2-(4-methylthiazol-5-yl)ethyl nitrate maleate salt | 30.00% | 4.55 |
| Methocel K100M | 35.75% | 5.42 |
| Avicel PH 102 | 23.50% | 3.56 |
| Povidone | 10.00% | 1.52 |
| Cab-O-Sil | 0.25% | 0.038 |
| Magnesium Stearate | 0.50% | 0.076 |
| Total | 100.00% | 15.17 |

| Component | % | g |
|---|---|---|
| 2-(4-methylthiazol-5-yl)ethyl nitrate maleate salt | 40.00% | 7.10 |
| Methocel K100M | 25.75% | 4.57 |
| Avicel PH 102 | 23.50% | 4.17 |
| Povidone | 10.00% | 1.78 |
| Cab-O-Sil | 0.25% | 0.044 |
| Magnesium Stearate | 0.50% | 0.089 |
| Total | 100.00% | 17.75 |

| Component | % | g |
|---|---|---|
| 2-(4-methylthiazol-5-yl)ethyl nitrate maleate salt | 40.00% | 7.10 |
| Ethocel 100 Premium | 25.75% | 4.57 |
| Avicel PH 102 | 23.50% | 4.17 |
| Povidone | 10.00% | 1.78 |
| Cab-O-Sil | 0.25% | 0.044 |
| Magnesium Stearate | 0.50% | 0.089 |
| Total | 100.00% | 17.75 |

Using a Korsch XL 100 Press, the formulations described above were pressed into a dry tablet for oral use. The maleate salt provided herein has processing advantages over other salts (e.g., the chloride, phosphate, mesylate, and sulfate salts) in the preparation of a dry tablet.

REFERENCES

Arancio, O., E. R. Kandel, R. D. Hawkins, "Activity-dependent long-term enhancement of transmitter release by presynaptic 3',5'-cyclic GMP in cultured hippocampal neurons", Nature 376 (1995) 74-80.

Barger, S. W., R. R. Riscus, P. Ruth, F. Hofmann, M. P. Mattson, "Role of cyclic GMP in the regulation of neuronal calcium and survival by secreted forms of .beta.-amyloid precursor protein", J. Neurochem. 64 (1995) 2087-2096.

Bernabeu, R. N. Schroder, J. Quevedo, M. Cammarota, I. Izquierdo, J. H. Medina, "Further evidence for the involvement of a hippocampal cGMP/cGMP-dependent protein kinase cascade in memory consolidation", NeuroReport 8 (1997) 2221-2224.

Bernabeu, R., P. Schmitz, M., P. Faillace, I. Izquierdo, J. H. Medina, "Hippocampal cGMP and cAMP are differentially involved in memory processing of inhibitory avoidance learning", NeuroReport 7 (1996) 585-588.

Briscoe et al., Am. J. Physiol. 1233 (1995) 134.

Bullock, R., A Zauner, J. J. Woodward, J. Nyseros, S. C. Choi, J. D. Ward, A. Marmarou, H. F. Young, "Factors affecting excitatory amino acid release following severe human head injury", J. Neurosurg. 89 (1998) 507-518.

Chan, P. H., M. Kawase, K. Murakami, S. F. Chen, Y, Li, B. Calagui, L. Reola, E. Carlson, C. J. Epstein, "Overexpression of SOD1 in transgenic rats protects vulnerable neurons against ischemic damage after global cerebral ischemia and reperfusion", J. Neurosic. 18 (1998) 8292-8299.

Chen, J., T. Nagayama, K. Jin, R. A. Stetler, R. L. Zhu, S. H. Graham, R. P. Simon, "Induction of caspase-3-like protease may mediate delayed neuronal death in the hippocampus after transient cerebral ischemia", J. Neurosci. 18 (1998) 4914-4928.

Cohen, G. M., "Caspases: the executioners of aopotosis", Biochem. J. 326 (1997) 1-16.

Du, Y., K. R. Bales, R. C. Dodel, E. Hamilton-Byrd, J. W. Horn, D. L. Czilli, L. K. Simmons, B. Ni, S. M. Paul, "Activation of a caspase-3-related cysteine protease is required for glutamate-mediated apoptosis of cultured cerebellar granule neurons", Proc. Natl. Acad. Sci. U.S.A. 94 (1997) 11657-11662.

Endres, M., S, Namura, M. Shimizu-Sasamata, C. Waebar, L. Zhang, T. Gomez-Isla, B. T. Hyman, M. A. Moskowitz, "Attenuation of delayed neuronal death after mild focal ischemia in mice by inhibition of the caspase family", J. Cereb. Blood Flow Metab. 18 (1998) 238-247.

Estevez, A. G., N. Spear, J. A. Thompson, T. L. Cornwell, R. Radi, L. Barbeito, J. S. Beckman, "Nitric oxide-dependent production of cGMP supports the survival of rat embryonic motor neurons cultured with brain-derived neurotrophic factor", J. Neurosci. 18 (1998) 3708-3714.

Farinelli, S. E., D. S. Park, L. A. Greene, "Nitric oxide delays the death of trophic factor-deprived PC12 cells and sympathetic neurons by a cGMP-mediated mechanism", J. Neurosci. 16 (1996) 23-25-2234.

Furukawa, K., S. W. Barger, E. M. Blalock, M. P. Mattson, "Activation of K.sup.+ channels and suppression of neuronal activity by secreted .beta.-amyloid precursor protein", Nature 379 (1996) 74-78.

Gaetani, P., A. Pasqualin, R. Rodriguez y Baena, E. Borasio, F. Marzatico, "Oxidative stress in the human brain after subarachnoid hemorrhage", J. Neurosurg. 89 (1998) 748-754.

Goda, H., H. Ooboshi, H. Nakane, S. Ibayashi, S. Sadoshima, M. Fujishima, "Modulation of ischemia-evoked release of excitatory and inhibitory amino acids by adenosine A1 receptor agonist", Eur. J. Pharmacol. 357 (1998) 149-155.

Gottron, F. J., H. S. Ying, D. W. Choi, "Caspase inhibition selectively reduces the apoptotic component of oxygen-glucose deprivation-induced cortical neuronal cell death", Mol. Cell. Neurosci. 9 (1997) 159-169.

Haviv, R., L. Lindenboim, H. Li, J. Yuan, R. Stein, "Need for caspases in apoptosis of trophic factor-deprived PC12 cells", J. Neurosci. Res. 50 (1997) 69-80.

Higashi et al., Neuropathol. Appl. Neurobiol. 21 (1995) 480-483.

Huang, F. P., L. F. Zhou, G. Y. Yang, "Effects of mild hypothermia on the release of regional glutamate and glycine during extended transient focal cerebral ischemia in rats", Neurochem. Res. 23 (1998) 991-996.

Ibarrola, D., H. Seegers, A. Jaillard, M. Hommel, M. Decorps, R. Massarelli, "The effect of eliprodil on the evolution of a focal cerebral ischaemia in vivo", Eur. J. Pharmacol. 352 (1998) 29-35.

Jiang et al., J. Cereb. Blood Flow Metab. 18 (1998) 758-767.

Kesner, NIDA Res. Monographs 97 (1990) 22-36.

Kim, Y. M., R. V. Talanian, T. R. Billiar, "Nitric oxide inhibits apoptosis by preventing increases in caspase-3-like activity via two distinct mechanisms", J. Biol. Chem. 272 (1997) 31138-31148.

Louw, R., H. P. W. Vermeeren, J. J. A. Van Asten, W. J. Ultee, J. Chem. Soc., Chem. Comm. (1976) 496-497

Macdonald, R. L., M. Stoodley, "Pathophysiology of cerebral ischemia", Neurol. Med. Chir. (Tokyo) 38 (1998) 1-11.

Mattson and Scheff, J. Neurotrauma 11 (1994) 3-33.

Mizuno, A., K. Umemura, M. Nakashima, "Inhibitory effect of MCI-186, a free radical scavenger, on cerebral ischemia following rat middle cerebral artery occlusion", Gen. Pharmacol. 30 (1998) 575-578.

Mordenti, "Man versus beast: Pharmacokinetic scaling in mammals", J. Pharm. Sci. 75 (1986) 1028-1040.

Morgan et al., "Approaches to the discovery of non-peptide ligands for peptide receptors and peptidases", In Ann. Rep. Med. Chem. (Virick F. J., et al.) (1989) pp. 243-253, Academic Press, San Diego, Calif.

Namura, S., J. Zhu, K. Fink, M. Endres, A Srinivasan, K. J. Tomaselli, J. Yuan, M. A. Moskowitz, "Activation and cleavage of caspase-3 in apoptosis induced by experimental cerebral ischemia", J. Neurosci. 18 (1998) 3659-3668.

Ni, B., X. Wu, Y. Su, D. Stephenson, E. B. Smalstig, J. Clemens, S. M. Paul, "Transient global forebrain ischemia induces a prolonged expression of the caspase-3 mRNA in rat hippocampal CA1 pyramidal neurons", J. Cereb. Blood Flow Metab. 18 (1998) 248-256.

Nicholson, D. W., N. A. Thornberry, "Caspases: killer proteases", Trends Biochem. Sci. 22 (1997) 299-306.

O'Neill, M. J., A. Bond, P. L. Ornstein, M. A. Ward, C. A. Hicks, K. Hoo, D. Bleakman, D. Lodge, "Decahydrosioquinolines: novel competitive AMPA/kainate antagonists with neuroprotective effects in global cerebral ischaemia", Neuropharmacol. 37 (1998) 1211-1222.

Ouellette, R. J., R. J. Bertsch, J. Org. Chem. 41 (1976) 2782-2783.

Owais, M. et al., Antimicrob. Agents Chemother. 39 (1995) 180.

Ranade, V. V., J. Clin. Pharmacol. 29 (1989) 685.

Tagami, M. K. Yamagata, K. Ikeda, Y. Nara, H. Fujino, A. Kobota, F. Numano, Y. Yamori, "Vitamin E prevents apoptosis in cortical neurons during hypoxia and oxygen reperfusion", Lab. Invest. 78 (1998) 1415-1429.

Umemura, K., A. Shimakura, M. Nakashima, "Neuroprotective effect of a novel AMPA receptor antagonist, YM90K, in a rat focal cerebral ischaemia", Brain Res. 773 (1997) 61-65.

Umezawa et al., Biochem. Biophys. Res. Commun. 153 (1988) 1038.

Venault, P. G. Chapouthier, L., Prado de Carvalho and Rossier, J., Encephale, 18 (1992) 655.

Wittkowsky, Pharmacotherapy 18 (1998) 945-1005.

Wu, J., Y. Wang, M. J. Rowan, R. Anwyl, "Evidence for involvement of the cGMP-protein kinase G signaling system in the induction of long-term depression, but not long-term potentiation, in the dentate gyrus in vitro", J. Neurosci. 18 (1998) 3589-3596.

Yang, K., J. D. Artz, J. Lock, C. Sanchez, B. M. Bennett, A. B. Fraser, G. R. Thatcher, J. Chem. Soc., Perkin Trans. 1 (1996) 1073-1075.

Yang, Y. L., W. H. Pan, T. H. Chiu, M. T. Lin, "Striatal glutamate release is important for development os ischemic damage to strital neurons during rat heatstroke", Brain Res. 795 (1998) 121-127.

The invention claimed is:

1. The maleate salt of the compound

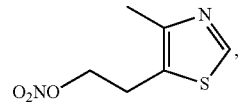

having the XRPD graphic scan of FIG. 1.

2. A pharmaceutical composition comprising the maleate salt of the compound

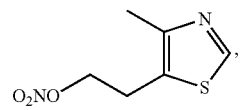

having the XRPD graphic scan of FIG. 1, together with a pharmaceutically acceptable diluent or carrier.

3. A dry tablet composition comprising the maleate salt of the compound

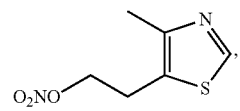

having the XRPD graphic scan of FIG. 1, and a pharmaceutically acceptable diluent or carrier.

4. The dry tablet of claim 3, formulated for oral administration.

5. A method for inhibiting neurodegeneration in a subject in need thereof, said method comprising administering to said subject an effective amount of the maleate salt of claim 1, such that said neurodegeneration is inhibited, wherein said neurodegeneration is associated with a condition selected from the group consisting of dementia and Alzheimer's disease.

6. The method of claim 5, wherein administering the therapeutic compound to said subject modulates levels of cyclic nucleotide cGMP and/or cAMP.

7. The method of claim 5, wherein said neurodegeneration is associated with dementia.

8. The method of claim 5, wherein said neurodegeneration is associated with Alzheimer's disease.

9. A method for effecting cognition enhancement in a subject in need thereof comprising administering to said subject an effective amount of the maleate salt of claim 1.

10. A method for mitigating cerebral damage due to ischemia in a subject in need thereof comprising administering to said subject an effective amount of the maleate salt of claim 1, such that cerebral damage is mitigated.

11. The method of claim 5, wherein said maleate salt is administered orally.

12. A method for inhibiting neurodegeneration in a subject in need thereof, said method comprising administering to said subject an effective amount of a composition of claim 2, such that said neurodegeneration is inhibited, wherein said neurodegeneration is associated with a condition selected from the group consisting of dementia and Alzheimer's disease.

13. A method for inhibiting neurodegeneration in a subject in need thereof, said method comprising administering to said subject an effective amount of a composition of claim 3, such that said neurodegeneration is inhibited, wherein said neurodegeneration is associated with a condition selected from the group consisting of dementia and Alzheimer's disease.

14. A method for inhibiting neurodegeneration in a subject in need thereof, said method comprising administering to said subject an effective amount of a composition of claim 4, such that said neurodegeneration is inhibited, wherein said neurodegeneration is associated with a condition selected from the group consisting of dementia and Alzheimer's disease.

15. The method of claim 9, wherein said composition is administered orally.

16. The method of claim 10, wherein said composition is administered orally.

* * * * *